United States Patent [19]

Plevnik et al.

[11] 4,387,719
[45] Jun. 14, 1983

[54] CONTROL CIRCUIT OF A THERAPEUTIC STIMULATOR FOR THE URINARY INCONTINENCE

[75] Inventors: Stanislav Plevnik, Brezovica pri Ljubljani; Peter Vrtacnik, Kamnik; Matija Malezic, Ljubljana; Marino Lukezic, Portorož; Uros Stanic; Pavel Oblak, both of Ljubljana, all of Yugoslavia

[73] Assignee: Gorenje Tovarna Gospodinjske Opreme N.Sol.O. Velenje, Valenje, Yugoslavia

[21] Appl. No.: 314,455

[22] Filed: Oct. 23, 1981

[30] Foreign Application Priority Data

Oct. 23, 1980 [YU] Yugoslavia ............................ 2725/80

[51] Int. Cl.³ ............................................. A61N 1/36
[52] U.S. Cl. ................................ 128/421; 128/419 E
[58] Field of Search ............ 128/419 E, 420 R, 421 R, 128/422, 423, 788, DIG. 25

[56] References Cited

U.S. PATENT DOCUMENTS

| | | | |
|---|---|---|---|
| 3,403,684 | 10/1968 | Stibel | 128/788 |
| 3,835,833 | 9/1974 | Limoge | 128/420 R |
| 3,870,051 | 3/1975 | Brindley | 128/419 E |
| 3,983,881 | 10/1976 | Wickham | 128/422 |
| 4,038,991 | 8/1977 | Walters | 128/419 PG |
| 4,324,253 | 4/1982 | Greene et al. | 128/421 |

*Primary Examiner*—William E. Kamm
*Attorney, Agent, or Firm*—Fleit, Jacobson & Cohn

[57] ABSTRACT

In the control circuit of a therapeutic stimulator for the urinary incontinence, whereby the sphincter of the urethra is stimulated and at the same time a reflected inhibition of the urinary bladder is caused, stimulation pulses are generated. The circuit enables an automatic interruption of stimulation pulses after predetermined periods of time, or a continuous operation.

1 Claim, 1 Drawing Figure

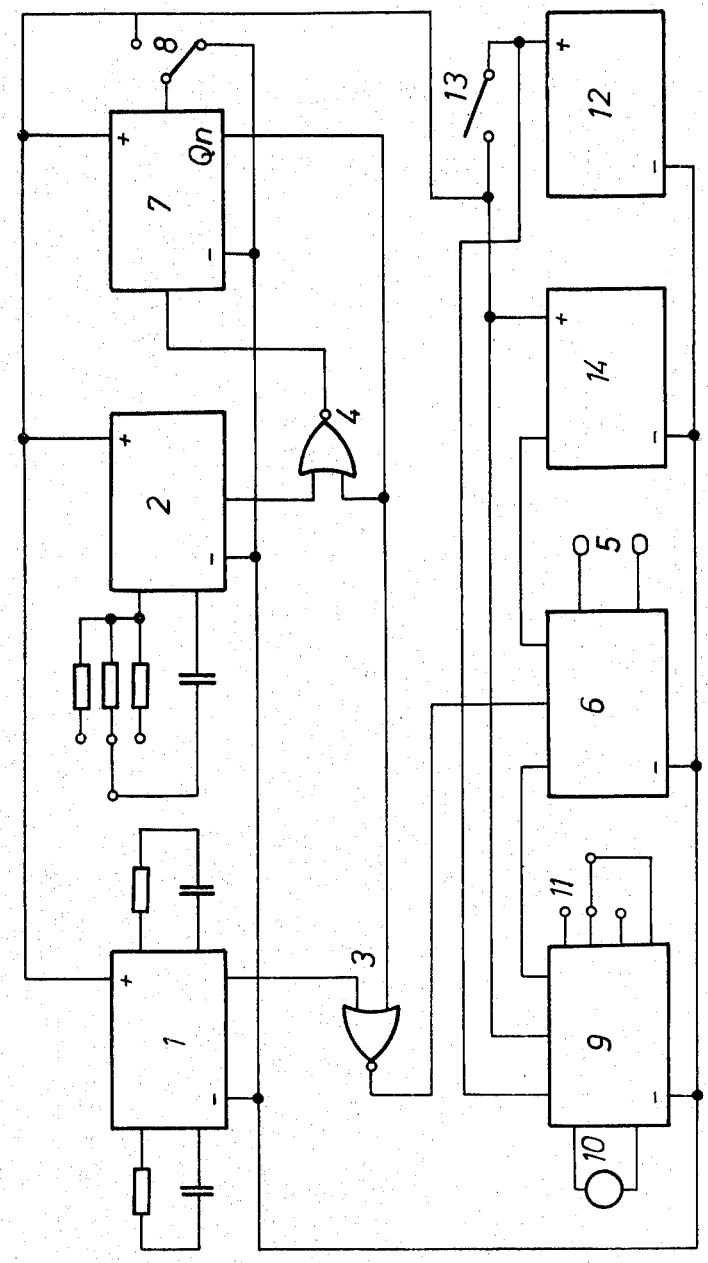

CONTROL CIRCUIT OF A THERAPEUTIC STIMULATOR FOR THE URINARY INCONTINENCE

Object of the invention is a control circuit of a therapeutic stimulator for the urinary incontinence, which is used as a therapeutic aid at patients with urinary incontinence. Thereby the sphincter of the urethra is stimulated and at the same time a reflected inhibition of the urinary bladder is caused.

Known are embodiments of control circuits for an automatic interruption of operation after predetermined periods of time, which are either limited regarding the manner of operation thereof, or the technical performances to be met. Such control circuits are constructed as independent units, the electronic circuits are complicated constructions, the connection with the existing electronic sub-assemblies usually also requesting corresponding adjustments. Because of their voluminosity and complicated construction the reliability of operation is reduced and simple handling is rendered impossible.

It is the aim of the invention to realize a control circuit of a therapeutic electric stimulator, which enables an automatic interruption of stimulation pulses after predetermined periods of time, or a continuous operation. The control circuit should in a simple manner interconnect known electronic circuits, such as the pulse generator and the final stage with electrodes, which increases the reliability of operation of the whole stimulator and enables simple handling.

The aim as set was attained by an electronic construction of the control circuit, which in simple manner interconnects known electronic circuits, which enables an automatic interruption of stimulation pulses after predetermined periods of time, or a continuous operation.

The invention is elucidated in detail on the basis of an embodiment and the corresponding drawing showing the electric diagram of the circuit according to the invention.

As is shown in the drawing, the pulse generator 1 is with its output over the NOR gate 3 connected to the input of the final stage 6, which amplifies the pulses and leads them to the stimulation electrodes 5. The fundamental frequency generator 2 made as an astable multivibrator with the possibility of varying the circuit frequency at a constant pulse width is with its output over the NOR gate 4 connected to the input of the binary counter 7, the "reset" input of which is over the switch 8 connected to the positive or negative pole of the supply. The output $Q_n$ of the binary counter 7 is connected to the inputs of the NOR gate 3 and NOR gate 4.

The operation of the control circuit according to the invention is as follows. The output of the pulse generator 1 is over the NOR gate 3, to which is also connected the output $Q_n$ of the binary counter 7, connected to the input of the final stage 6 provided with stimulation electrodes 5. The output of the fundamental frequency generator 2 oscillating with various frequencies is over the NOR gates 4, to which is also connected the output $Q_n$ of the binary counter 7, connected to the input of the binary counter 7 which divides the fundamental frequency in binary mode. When the switch 8 connected to the "reset" input of the binary counter 7 is connected to the negative pole of the supply, the binary counter 7 counts $2^n$ pulses from the fundamental frequency generator 2, and by the logic state "1" on the output $Q_n$ connected to the inputs of the NOR gates 3, 4 interrupts the transfer of stimulation pulses from the pulse generator 1 to the input of the final stage 6 provided with stimulation electrodes 5, and the transfer of pulses from the fundamental frequency generator 2 to the input of the binary counter 7. By switching the switch 8 connected to the "reset" input of the binary counter 7 to the positive pole of the supply, the output $Q_n$ of the binary counter 7 is set into the logic state "0", which enables a permanent transfer of stimulation pulses from the pulse generator 1 over the NOR gate 3 to the input of the final step 6 provided with stimulation electrodes 5, and the transfer of pulses from the fundamental frequency generator 2 over the NOR gate 4 to the input of the binary counter 7.

The stimulator according to the invention also comprises a stimulator-operator-testing circuit 9 with a light indicator 10 which is switched to different inputs of the circuit 9 by a three positional switch 11. In such manner, by the indicator 10 the charging step of the supply batteries 12, the switching on of the stimulator according to the invention, which is realized over the switch 13, and the operation of the final stage 6, which is supplied over the converter 14, are tested. The units 9 to 14 which are important for the operation of the stimulator according to the invention do not represent the object of the invention and are not covered by the scope of patent protection.

What is claimed is:

1. Control circuit of a therapeutic stimulator for the urinary incontinence, characterized in that the output of the pulse generator (1) is connected to the first input of the NOR gate (3), the second input of which is connected to the output ($Q_n$) of the binary counter (7), the output thereof being connected to the input of the final stage (6) provided with stimulation electrodes (5), and that the output of the fundamental frequency generator (2) is connected to the first input of the NOR gate (4), the output thereof being connected to the input of the binary counter (7), the "reset" input of which is over the switch (8) connected to the positive or negative pole of the supply and the output ($Q_n$) being connected to the second input of the NOR gate (4).

* * * * *